(12) United States Patent
Dutova et al.

(10) Patent No.: US 7,045,177 B2
(45) Date of Patent: May 16, 2006

(54) SULFODERIVATIVES OF ACENAPHTHO[1,2-B]QUINOXALINE, LYOTROPIC LIQUID CRYSTAL AND ANISOTROPIC FILM ON THEIR BASE

(75) Inventors: Tatyana Y. Dutova, Moscow (RU); Alexey Y. Nokel, Moscow (RU); Elena N. Sidorenko, Moscow (RU); Sergey V. Timofeev, Moscow (RU)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 10/992,245

(22) Filed: Nov. 17, 2004

(65) Prior Publication Data

US 2005/0109986 A1 May 26, 2005

Related U.S. Application Data

(60) Provisional application No. 60/524,068, filed on Nov. 21, 2003.

(51) Int. Cl.
*C09K 19/52* (2006.01)
*C09K 19/54* (2006.01)
*C07D 24/38* (2006.01)

(52) U.S. Cl. .............. 428/1.1; 252/299.01; 252/299.5; 428/1.3; 428/1.31; 544/342

(58) Field of Classification Search ........... 252/299.01, 252/299.1, 299.5; 428/1.1, 1.31, 1.3; 544/342
See application file for complete search history.

(56) References Cited

U.S. PATENT DOCUMENTS

| | | | | |
|---|---|---|---|---|
| 5,739,296 A | * | 4/1998 | Gvon et al. | 534/577 |
| 5,959,107 A | * | 9/1999 | Ishiguro et al. | 544/284 |
| 6,174,394 B1 | * | 1/2001 | Gvon et al. | 156/100 |
| 6,563,640 B1 | * | 5/2003 | Ignatov et al. | 359/491 |
| 6,583,284 B1 | * | 6/2003 | Sidorenko et al. | 544/342 |
| 2003/0232153 A1 | * | 12/2003 | Nazarov et al. | 428/1.3 |
| 2004/0058091 A1 | * | 3/2004 | Dutova et al. | 428/1.1 |
| 2004/0215015 A1 | * | 10/2004 | Nazarov et al. | 544/14 |
| 2005/0195340 A1 | * | 9/2005 | Lazarev | 349/62 |
| 2005/0196550 A1 | * | 9/2005 | Lazarev et al. | 428/1.1 |
| 2005/0200771 A1 | * | 9/2005 | Lazarev et al. | 349/62 |

FOREIGN PATENT DOCUMENTS

WO WO 96/16015 A 5/1996
WO WO 2004/014874 A 2/2004

OTHER PUBLICATIONS

Werner, *Experimentelles,* Schiff und U. Monsaoohi, diese Annalen 288, 313 (1895), pp. 336-357.
von Paul Ruggli et al., *Uber ortho-Disazo und o,o'-Trisazofarbstoffe (III),* Basel, Anstalt fur organische Chemie, 2. VII. 34, (1932), pp. 973-992.
English translation of relevant parts of reference A and B.
Database Beilstein XP002322578 Database accession No. BRN 319493 abstract & Oliveri-Mandala: Atti Accad. Nax. Lincei Sci. Fis. Mat. Nat. Rend., vol. 5, No. 21, 1912, p. 782.
Database Caplus 'Online! Chemical Abstracts Service, Columbus, Ohio, US; Guha, S. K. et al: "Acenaphthophenazines" XP002322579 retrieved from STN Database accession No. 1972:128780 abstract & Journal of the Indian Chemical Society, 48(11), 1011-16 Coden: JICSAH; ISSN: 0019-4522, 1971.

* cited by examiner

*Primary Examiner*—Shean C. Wu
(74) *Attorney, Agent, or Firm*—Dorsey & Whitney LLP

(57) ABSTRACT

The present invention provides a series of new chemical compounds, lyotropic liquid crystal systems, materials, blends, mixtures, namely acenaphtho[1,2-b]quinoxaline sulfoderivatives of the general structural formula:

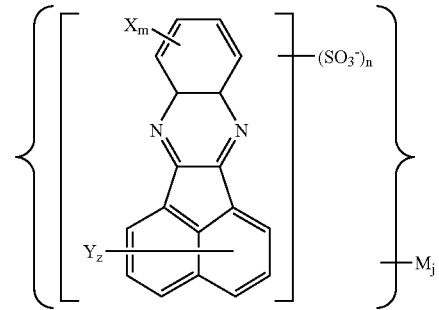

wherein n is an integer in the range of 1 to 4; m is an integer in the range of 0 to 4; z is an integer in the range of 0 to 6, and $m+z+n \leq 10$; X and Y are individually selected from the group consisting of $CH_3$, $C_2H_5$, $OCH_3$, $OC_2H_5$, Cl, Br, OH, $OCOCH_3NH_2$, $NHCOCH_3$, $NO_2$, F, $CF_3$, CN, OCN, SCN, COOH, and $CONH_2$; M is a counterion; and j is the number of counterions in the molecule.

27 Claims, 3 Drawing Sheets

SULFODERIVATIVES OF ACENAPHTHO[1,2-B]QUINOXALINE, LYOTROPIC LIQUID CRYSTAL AND ANISOTROPIC FILM ON THEIR BASE

CROSS REFERENCE TO RELATED APPLICATIONS

This application claims the benefit of, and priority to, of U.S. provisional patent application Ser. No. 60/524,068 filed on Nov. 21, 2003, entitled "Sulfoderivatives of Acenaphtho [1,2-b]quinoxaline, Lyotropic Liquid Crystals and Anisotropic Film on their Base" the entire disclosure of which is incorporated herein by reference.

FIELD OF THE INVENTION

The present invention generally relates to the field of organic chemistry and, in particular, optically anisotropic coatings. More specifically, the present invention is related to heterocyclic sulfoderivative compounds and manufacturing optically anisotropic coatings thereof.

BACKGROUND OF THE INVENTION

Modern technological progress requires development of optical elements based on new materials with specific, controllable properties. In particular, the necessary optical element in modern visual display systems is an optically anisotropic film that is optimized for the optical characteristics of an individual display module.

Various polymer materials are known in the prior art for use in the production of optically anisotropic films. Films based on these polymers acquire optical anisotropy through uniaxial extension and coloring with organic dyes or iodine. Polyvinyl alcohol is one commonly used polymer in this application. However, the low thermal stability of films based on polyvinyl alcohol limits their applications. Polyvinyl alcohol based films are described in greater detail in *Liquid Crystals—Applications and Uses*, B. Bahadur, ed., Vol. 1, World Scientific, Singapore, N.Y., July 1990, p. 101.

Organic dichroic dyes are a new class of materials currently gaining prominence in the manufacture of optically anisotropic films with desirable optical and working characteristics. Films based on these materials are formed by coating a liquid crystal (LC) aqueous solution of supramolecules formed by dye molecules on a substrate surface with subsequent water evaporation. The produced films are imbued with anisotropic properties either by preliminary mechanical ordering of the underlying substrate surface as described in U.S. Pat. No. 2,553,961 or by applying external mechanical, electromagnetic, or other orienting forces to the coating on a liquid crystal substrate material as described in U.S. Pat. Nos. 5,739,296 and 6,174,394.

Liquid crystalline behavior of dye solutions is known. However, exploitation these dye based liquid crystals for industrial applications, such as in liquid crystal displays (LCDs) and glazing, has raised great interest.

Supramolecules form a lyotropic liquid crystal (LLC). Substantial molecular ordering or organization of dye molecules in columns allows use of these supramolecular liquid crystal mesophases to create oriented, strongly dichroic films.

Dye molecules that form supramolecular liquid crystal mesophases are unique. These dye molecules contain functional groups located at the periphery and confers water soluble properties to the dye molecules. Organic dye mesophases are characterized by specific structures, phase diagrams, optical properties and solubility properties as described in greater detail in J. Lydon, Chromonics, in *Handbook of Liquid Crystals*, (Wiley V C H: Weinheim, 1998), V. 2B, p. 981–1007, incorporate herein by reference in its entirety.

Anisotropic films characterized by high optical anisotropy may be formed from LLC systems based on dichroic dyes. Such films exhibit both the properties of E-type polarizers, due to light absorption by supramolecular complexes, and the properties of retarders and compensators as described in related co-pending application entitled "Compensator for Liquid Crystal Display", U.S. provisional patent application Ser. No. 60/549,792 filed Mar. 2, 2004, the entire disclosure of which is hereby incorporated by reference. Retarders and compensators are films with phase-retarding properties in spectral regions where absorption is lacking. Phase-retarding or compensating properties of the films are determined by their double refraction properties known as birefringence ($\Delta n$):

$$\Delta n = |n_o - n_e|$$

expressed in terms of as the difference in refractive indices between the extraordinary wave ($n_e$) and the ordinary wave ($n_o$). Depending on the orientation of the molecules in a medium and the direction of the propagation, $n_e$ and $n_o$ varies. For example, if the direction of propagation coincides with the optical or crystal axis, ordinary polarization is predominantly observed. Whereas, if light propagates orthogonally or at some angle that is not orthogonal to the optical axis, the light emerging from the medium will separate and decompose into its extraordinary and ordinary wave components.

Usefully, in addition to optical properties, if high-strength dyes are used, films characterized by high thermal and photo stability can also be fabricated.

Extensive investigations aimed at developing new methods of fabricating dye-based films through manipulation of deposition conditions have been described in U.S. Pat. Nos. 5,739,296 and 6,174,394 and published patent application EP 961138. Of particular interest is the development of new compositions of lyotropic liquid crystals utilizing modifying, stabilizing, surfactant and/or other additives to known dyes, thereby, improving film characteristics.

The demands for producing anisotropic film with improved selectivity in different wavelength ranges are ever increasing. Films with different absorbance maxima over a wide spectral wavelength ranging from infrared to ultraviolet regions are needed for a variety of technological areas.

Hence, much recent research attention has been directed to the materials used in the manufacturing of isotropic and/or anisotropic double refraction films, polarizers, retarders or compensators, herein collectively known as optical materials or films, for LC displays and telecommunications applications, such as, for example, but not limited to those described by P. Yeh, *Optical Waves in Layered Media*, New York: John Wiley &Sons, Inc, 1998 and P. Yeh, and C. Gu, *Optics of Liquid Crystal Displays*, New York, John Wiley &Sons, Inc., 1999, incorporated herein by reference in their entirety. It has been found that ultra-thin double refraction films can be fabricated using known methods and technologies to produce optically anisotropic films composed of organic dye LLC systems. Recent reports on manufacturing of thin crystalline optically anisotropic films based on disulfoacids of the red dye Vat Red 14 has been described by Lazarev, P. and Paukshto, M., "Thin Crystal Film Retarders," 2000, *Proceeding of the 7th International Display Workshops, Materials and Components*, Kobe, Japan, November 29–December 1, pp.1159–1160, as cis- and trans-isomeric mixtures of naphthalenetetracarboxylic acid dibenzimidazole:

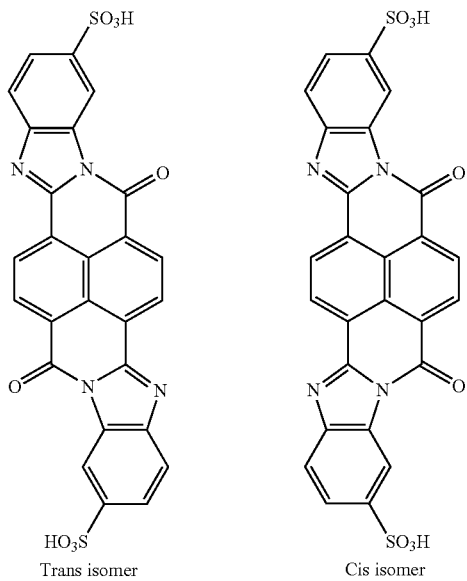

Trans isomer        Cis isomer

This technology permits control of the direction of the crystallographic axis of a film during coating and crystallization of the LC molecules on a substrate such as glass plates. The deposited films are uniform in composition and have high molecular and/or crystal ordering with a dichroic ratio, $\kappa_d$, of approximately 28, making them useful as optical materials or films such as, but not limited to, polarizers, retarders, double refraction materials (e.g., birefringent film) or compensators.

Now referring to FIG. 1, molecularly oriented red dye based films typically exhibit high anisotropy characterized by a large difference in the refractive indices, i.e., $\Delta n = n_o - n_e$, that varies 0.4 to 0.9 over wavelengths in the range of approximately 500 to −700 nm. However, their application is limited because the films operate in a narrow region of the visible spectrum, namely the green spectral region, where the dye does not show significant absorption.

Thin, double refraction films that are transparent in the visible region have been prepared based on sodium chromoglycate (DSCG):

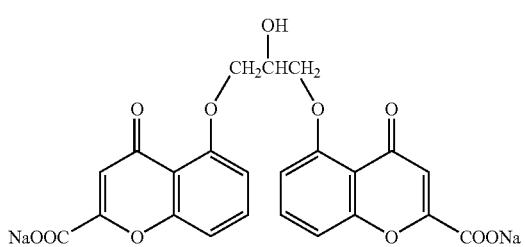

The anisotropy of the oriented film from DSCG is not very high. The difference in the refractive indices An is in the range of approximately 0.1 to 0.13. However, the thickness of the films based on DSCG can be varied over a wide range, thus allowing preparation of films with a desired phase-retarding effect despite the low anisotropic characteristics of the film. These films are discussed in greater detail in T. Fiske, et al., "Molecular Alignment in Crystal Polarizers and Retarders", *Society for Information Display, Int. Symp. Digest of Technical Papers*, Boston, Mass., May 19–24, pp. 566–569, 2002, incorporated herein by reference in entirety. The main disadvantage in many of these films lies in their dynamic instability, which leads to gradual recrystallization of the LC molecules and anisotropy degradation.

Other anisotropic materials have been synthesized based on water-soluble organic dyes utilizing the above-mentioned technology, see, e.g., U.S. Pat. Nos. 5,739,296 and 6,174,394 and European patent EP 0961138. These materials exhibit high absorbance in the visible spectral region, while advantageous for many applications it limits their application for forming transparent double refraction films.

Thus, there is a general need for films that are optically anisotropic and sufficiently transparent in the regions in which they operate. There exist needs for films for optics that are transparent in the visible range. It is therefore desirable to provide improved methods for synthesizing and preparing anisotropic films. It is also desirable to provide films for optics that are resistant to changes in temperature.

SUMMARY OF THE INVENTION

In general, the present invention provides a series of new chemical compounds, namely acenaphtho[1,2-b]quinoxaline sulfoderivatives having the general structural formula

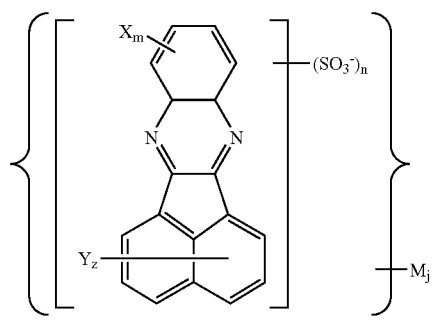

wherein n is an integer in the range of 1 to 4; m is an integer in the range of 0 to 4; z is an integer in the range of 0 to 6, $m+z+n \leq 10$; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$; M is a counter ion; and j is the number of counter ions in the molecule.

In another embodiment a lyotropic liquid crystal system is provided comprising at least one acenaphtho[1,2-b]quinoxaline sulfoderivatives having the structure of any one or combination of:

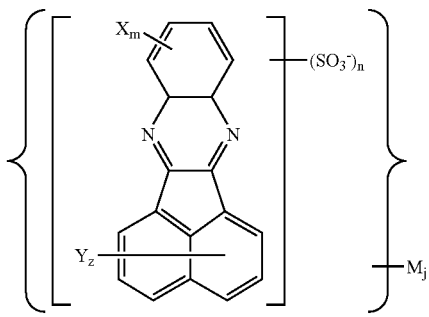

wherein n is an integer in the range of 1 to 4; m is an integer in the range of 0 to 4; z is an integer in the range of 0 to 6, m+z+n≦10; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$; M is a counter ion; and j is the number of counter ions in the molecule.

In yet a further aspect, a method of forming an optically anisotropic film is provided.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF THE DISCLOSED EMBODIMENTS

In one aspect, the present invention relates to compounds and methods for generating optical materials. In particular, the optical materials are either non-absorbing or only weakly absorbing in the visible spectral range. In another aspect, the optical materials are capable of forming a lyotropic liquid crystal (LLC) phase having enhanced stability for producing anisotropic at least partially crystalline films with high birefringence as illustrated in FIG. 2.

We have found that water-soluble compounds of the present invention, for example, acenaphtho[1,2-b]quinoxaline sulfoderivatives, address the identified problems herein. Methods for synthesizing sulfoderivatives of the present invention are described below.

Figure 1:
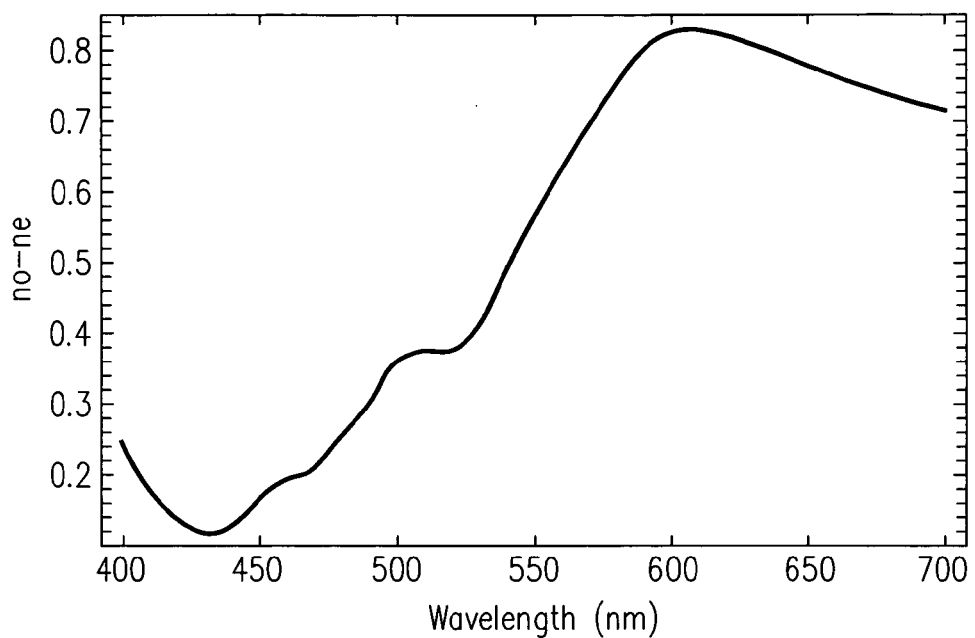
FIG. 1 illustrates the relationship between retardation or birefringence (Δn), and wavelength for film formed from sulfonated naphthalenetetracarboxylic acid dibenzimidazole as shown in the prior art.
Figure 2:
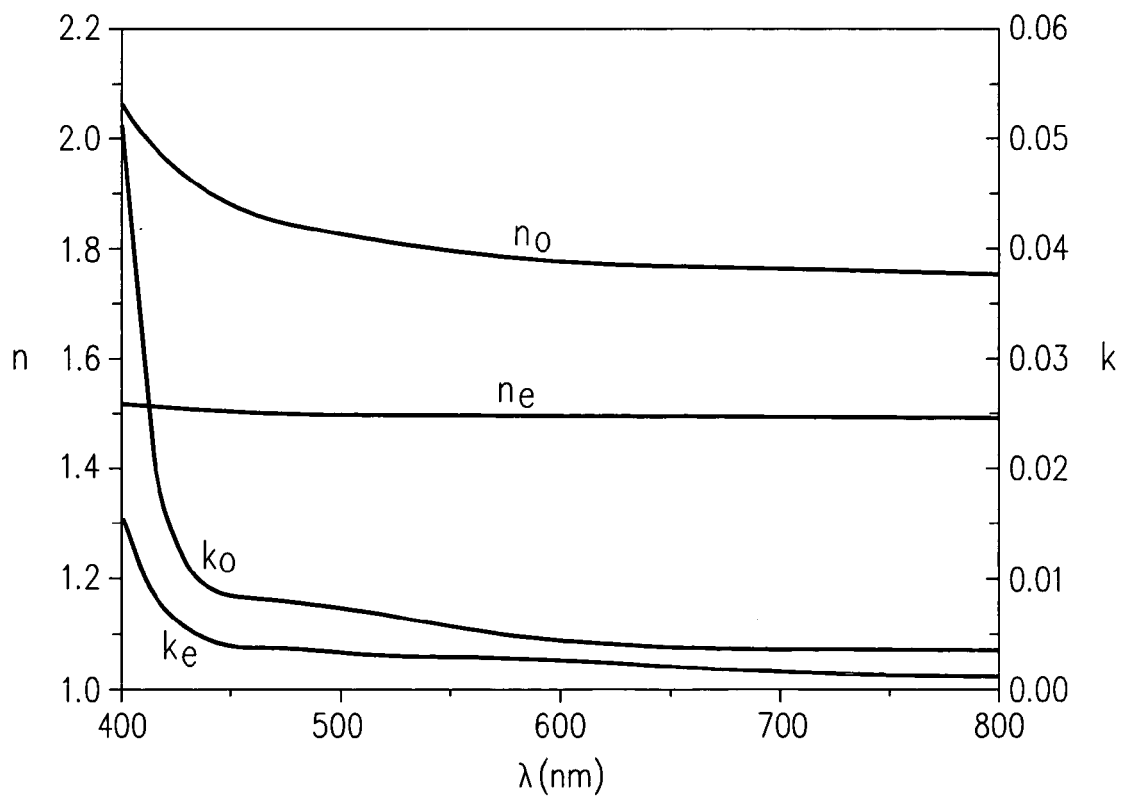
FIG. 2 shows a plot of absorption coefficients ($k_e$, $k_o$) for an acenaphtho[1,2-b]quinoxaline sulfonate system of the present invention versus wavelength that has been superimposed onto a plot illustrating the change in the extraordinary refractive index, measured parallel to the alignment direction, and ordinary refractive index, measured perpendicular to the alignment direction, over the same range of wavelength

Now referring to FIG. 2, the optical material of an exemplary embodiment of the present invention is indeed birefringent, i.e., the values for $n_e$ and $n_o$ are clearly different. Over the defined wavelength region, the magnitude of birefringence ranges from 0.2 to 0.4.

Figure 3:
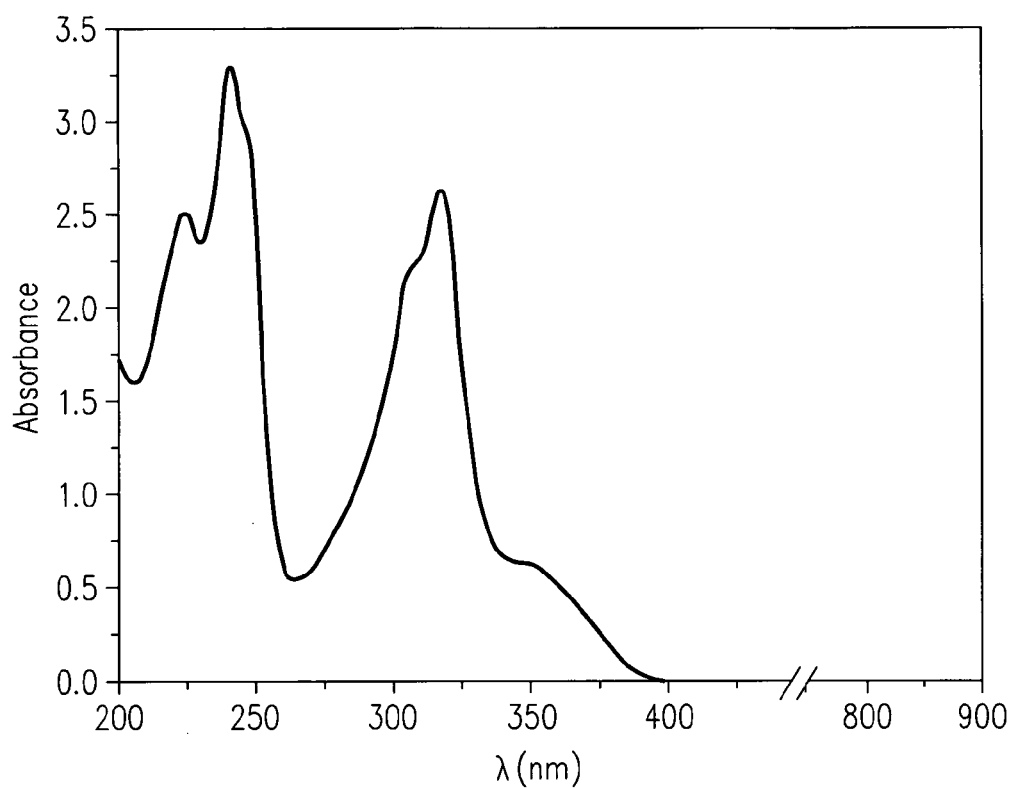
FIG. 3 is an absorption spectrum for an aqueous solution of one contemplated acenaphtho[1,2-b]quinoxaline sulfonate system of the present invention having a concentration 25 mg/L.

Still referring to FIG. 2, the optical material is sufficiently transparent over a substantial portion of the visible region. Above approximately 430 nm, the absorption coefficients parallel ($k_e$) and perpendicular ($k_o$) to the direction of alignment are nominal at most. Acenaphtho[1,2-b]quinoxaline and its derivatives do not possess well developed π-electron conjugated system as other known dichroic dyes. Thus, they absorb only in the UV spectral region and either do not or only weakly absorb in the visible spectral region. Therefore, as illustrated in FIG. 3, the sulfonated derivatives of acenaphtho[1,2-b]quinoxaline generally exhibit absorption maxima at approximately about λ≈245 and 320 nm.

In one aspect of the present invention, sulfoderivatives of acenaphtho[1,2-b]quinoxaline provide lyotropic liquid crystal (LLC) phases with enhanced stability over a wide range of concentrations, temperatures and pH ranges. These LLC phases are formed from organic compounds that ease the film formation process and can be coated with standard equipment for coating, thereby facilitating production of films without expensive and complex instruments under reproducible parameters.

In another aspect, the organic compounds or mixtures thereof of the present invention comprising at least one sulfoderivative, having an optimal hydrophilic-hydrophobic balance, is provided. This, in turn, affects the size and shape of the resultant supramolecules and the molecular ordering rate in the supramolecule itself, thus allowing the attainment of molecules or supramolecular structures having the desired solubility property. Proper solubility values promote high stability of the produced LLC phases. As a result, reproducibility of the film is improved and simplifies manufacturing by reducing the requirements for choosing and controlling technological conditions at different stages of the film formation. Furthermore, the optical performance of the produced films is improved by the increased uniformity in alignment of the acenaphtho[1,2-b]quinoxaline sulfoderivatives supramolecules on the substrate.

In still another embodiment of the present invention, colorless or weakly absorbing optical films are provided that may be used as, for example, a UV/VIS polarizer, retarder, compensator, or birefringent (double-refraction) material. Advantageously, high optical anisotropy (e.g., up to Δn=0.6 in the visible spectral range) and high transparency (e.g., extinction coefficients in the order of $10^{-3}$) of the films allow efficient single layered and multilayered reflective polarizer can be designed. Usefully, this reflective polarizer, in comparison with conventional one in which birefringent layers are made of stretched polymer film, see, e.g., Wortman D. L., "A Recent Advance in Reflective Polarizer Technology" (1997), *Research Conf. and International Workshops on LCD Tech. And Emissive Tech., SID*, 1997, M98–M106, is that the present invention can provide highly birefringent layers with a thickness of approximately about 100 nm. This ensures higher reflectivity and dichroic ratio than relatively low birefringent polymer films having the same number of layers.

In one embodiment, the water-soluble compounds of the present invention comprise acenaphtho[1,2-b]quinoxaline sulfoderivatives, represented by the general structural formula:

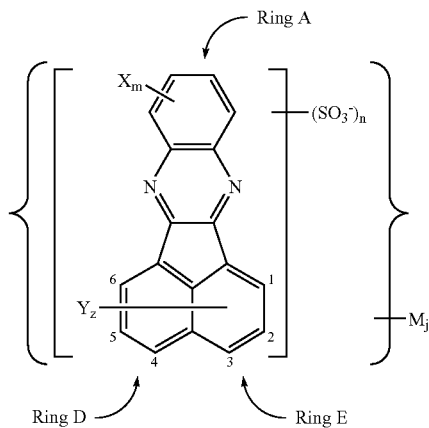

wherein:

n is an integer in the range of 1 to 4;

m is an integer in the range of 0 to 4;

z is an integer in the range of 0 to 6, subject to the restriction that $m+z+n \leq 10$;

X and Y are individually selected from $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;

M is a counterion; and j is the number of counterions in a molecule.

In the case where one counterion belonging to several molecules, j may be a fraction. If n is greater than 1, the counterions may be different. Counterions can be organic cations, such as, but not limited to, $NR_4^+$, where R is an alkyl, cycloalkyl or combination thereof, or inorganic cations, such as, but not limited to, $H^+$, $NH_4^+$, $\kappa^+$, $Li^+$, $Na^+$, $Cs^+$, $Ca^{++}$, $Sr^{++}$, $Mg^{++}$, $Co^{++}$, $Mn^{++}$, $Zn^{++}$, $Cu^{++}$, $Pb^{++}$, $Fe^{++}$, $Ni^{++}$, $Al^{+++}$, $Ce^{+++}$, $La^{+++}$, etc., or combinations thereof, including mixtures of organic and/or inorganic counterions thereof.

Now referring to the general structural formula hereinabove, a skilled artisan would understand from the depiction of $X_m$ that m number of X can reside anywhere or in any combination within the ring arbitrarily designated as A. Similarly, a skilled artisan would understand from the depiction of $Y_z$ that z number of Y can be substituted anywhere or in any combination within rings arbitrarily designated as D and E. Also, n number of $SO_3^-$ groups can reside on rings A, D and E in any combination. Depiction of these and other substituents in chemical structures in like manner herein should be similarly interpreted.

In one embodiment of the present invention comprise acenaphtho[1,2-b]quinoxaline sulfoderivatives of the general structural formula:

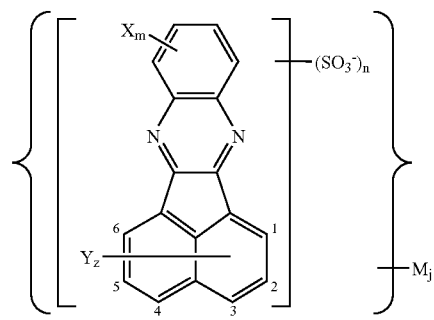

wherein:

n is an integer in the range of 1 to 4;

m is an integer in the range of 0 to 4;

z is an integer in the range of 0 to 6 and $m+z+n \leq 10$; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;

M is a counterion; and j is the number of counterions in the molecule, with the proviso that when n=1 and SO3— occupies position 1, then $m \neq 0$ or $z \neq 0$.

In one aspect, compounds comprising substantially one individual acenaphtho[1,2-b]quinoxaline sulfoderivative, suitable exemplary sulfoderivatives include, but are not limited to, compounds of structural formulas I, IIA–VIII, and these structural formulas differ by the number and positions of sulfo-, X- and Y-groups:

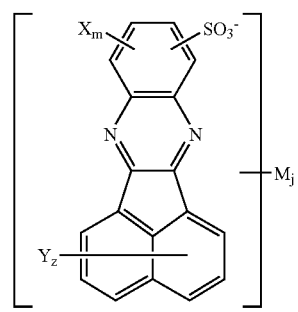

where m is an integer in the range of 0 to 3
and z is an integer in the range of 0 to 6;

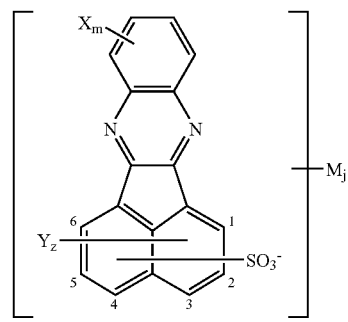

where m is an integer in the range of 0 to 4
and z is an integer in the range of 0 to 5,
with the proviso that when n = 1 and SO3-
occupies position 1, then $m \neq 0$ or $z \neq 0$.

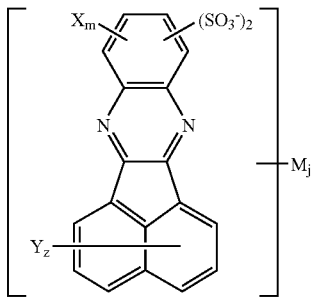

where m is an integer in the range of 0 to 2
and z is an integer in the range of 0 to 6;

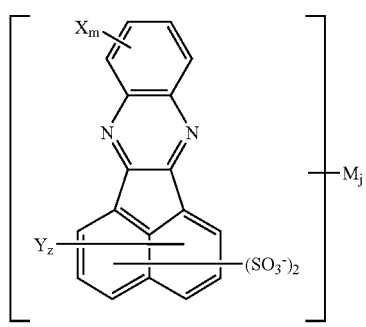

where m is an integer in the range of 0 to 4
and z is an integer in the range of 0 to 4;

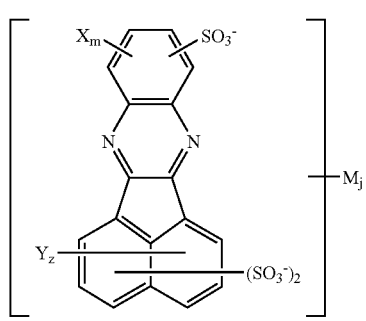

where m is an integer in the range of 0 to 3
and z is an integer in the range of 0 to 5;

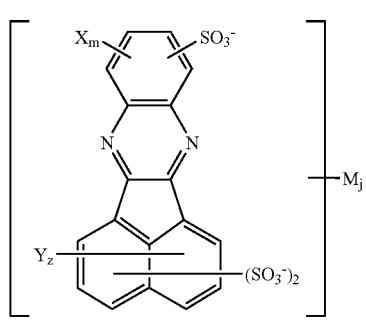

where m is an integer in the range of 0 to 3
and z is an integer in the range of 0 to 4;

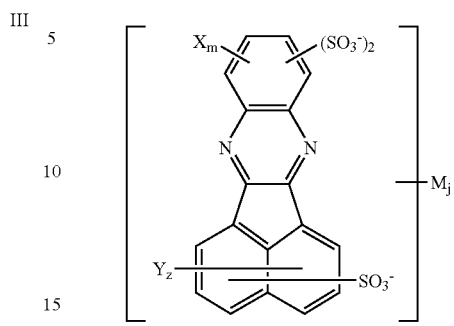

where m is an integer in the range of 0 to 2
and z is an integer in the range of 0 to 5;

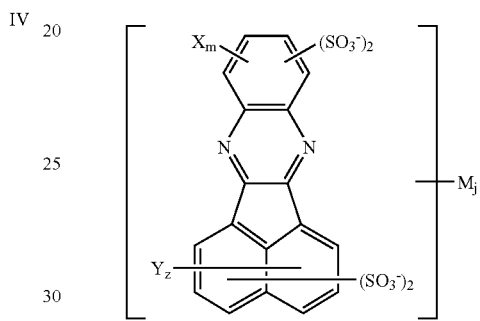

where m is an integer in the range of 0 to 2
and z is an integer in the range of 0 to 4;

For each structure I, IIA–VIII, X- and Y-groups are each independently selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$; M is a counterion; and j is the number of counterions in molecule. In the case where one counterion can belong to several molecules, j may be fractional. If the number of sulfo-groups is greater than 1, the individual counterions can be different.

Optionally, sulfoderivatives of the present invention can be blended or mixed together and/or in any combination with other known dichroic dyes, organic compounds that do not absorb in the visible region and/or capable of forming stable LLC phases, surfactants, additives, stabilizers, modifiers or plasticizers to form a liquid crystal system or composition. In certain embodiments, the system, composition or mixture of sulfoderivatives form a LLC phase. After solvent removal, the resultant LLC phase may form partially crystalline anisotropic films with favorable optical characteristics and high birefringence. Various cations, including for instance those selected from $H^+$, $N^+H_4$, $K^+$, $Li^+$, $Na^+$, $Cs^+$, $Ca^{++}$, $Sr^{++}$, $Mg^{++}$, $Ba^{++}$, $Co^{++}$, $Mn^{++}$, $Zn^{++}$, $Cu^{++}$, $Pb^{++}$, $Fe^{++}$, $Ni^{++}$, $Al^{+++}$, $Ce^{+++}$, $La^{+++}$ and others as well as mixtures of cations may be used as counterions in the structures I–VIII described above.

In another aspect of the invention, lyotropic liquid crystal systems are provided comprising at least one acenaphtho[1,2-b]quinoxaline sulfoderivative of the general structural formula:

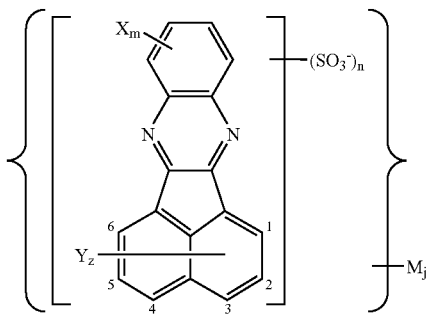

wherein:

n is an integer in the range of 1 to 4;

m is an integer in the range of 0 to 4;

z is an integer in the range of 0 to 6 and m+z+n≦10; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;

M is a counterion; and j is the number of counterions in the molecule.

Advantageously, the present invention provides LLC systems that are water-based composition comprising an individual acenaphtho[1,2-b]quinoxaline sulfoderivative of the general structural formula, disclosed herein, or mixtures of the sulfoderivatives. Such a LLC system, according to one contemplated embodiment of the present invention, is a mixture of water and organic compound miscible with water at any ratios or restrictedly miscible with water. In another exemplary embodiment, the LLC system comprises acenaphtho[1,2-b]quinoxaline sulfoderivatives or their mixtures in the range of approximately 3% to 60% by mass. In various exemplary embodiments, the LCC comprises acenaphtho[1,2-b]quinoxaline sulfoderivatives or their mixtures in the range of approximately 7% to 30% by mass. In certain exemplary embodiments, the LLC system may also comprise up to approximately 30% of surfactants and/or 30% of plasticizers.

In the LLC systems, depending on the required properties, the content of an individual acenaphtho[1,2-b]quinoxaline sulfoderivative may vary according to the following criteria:

1. monosulfoderivatives of the general structural formula having a mass concentration in the range of approximately 0% to 99% and more preferably can each or collectively have a mass concentration in the range of approximately 50% to 99%;
2. Disulfoderivatives of the general structural formula each or collectively having a mass concentration in the range of approximately 0 to 99% and more preferably can each or collectively have a mass concentration range of, approximately 50% to 99%;
3. Trisulfoderivatives of the general structural formula each or collectively having a mass concentration in the range of approximately 0% to 30% and more preferably can each or collectively have a mass concentration in the range of approximately 10% to 20%; or
4. Tetrasulfoderivatives of the general structural formula with mass concentration in the range of approximately 0% to 20% and more preferably can have a mass concentration in the range of approximately 5 to 10%.

The LLC systems may additionally comprise at least one water-soluble colorless organic compound or organic dye capable of participating in the LLC phase formation. Alternatively, the LLC system may additionally comprise at least two compounds of the general structural formula disclosed herein with at least two different substituents X and/or Y or at least one kind of substituents at two different locations.

Now referring again to FIG. 3, sulfoderivatives of acenaphtho[1,2-b]quinoxaline generally have absorption maxima in aqueous solutions in the near UV region at wavelengths approximately λ≈245 and 320 nm. The introduction of substituents such as ethyl, methyl, chlorine, and bromine does not generally cause considerable absorption band shift, compared to the same molecule without corresponding substituents. However, the introduction of amino and hydroxy substituents causes broadening in the absorption band and induces a shift into the long-wave region.

Usefully, varying the number of sulfo-groups and/or the number and character of the X- and/or Y-substituents in acenaphtho[1,2-b]quinoxaline, the hydrophilicity and hydrophobicity as well as the aggregative tendencies and overall viscosity of the liquid crystal (LC) solutions can be modified. Accordingly, the present invention provides compounds and method for creating films having suitable properties for optics by modifying the number and choice of peripheral substituents.

In one aspect, the acenaphtho[1,2-b]quinoxaline sulfoderivatives of the present invention forms optically anisotropic films.

In another aspect of the invention, optical films are provided comprising a mixture, composition or system of sulfoderivatives of the general formula:

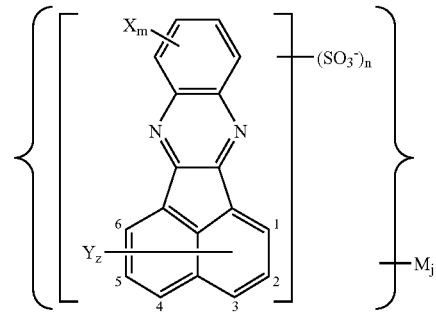

wherein:

n is an integer in the range of 1 to 4;

m is an integer in the range of 0 to 4;

z is an integer in the range of 0 to 6 and m+z+n≦10; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;

M is a counterion; and j is the number of counterions in the molecule.

In another aspect, the acenaphtho[1,2-b]quinoxaline sulfoderivatives of the present invention are capable of forming stable LLC systems. These acenaphtho[1,2-b]quinoxaline sulfoderivatives are suited for manufacturing optically isotropic or anisotropic films. In yet another aspect, the acenaphtho[1,2-b]quinoxaline sulfoderivatives are intended for producing at least partially crystalline films and/or UV/VIS polarizing and/or double-refraction (birefringent) films and materials.

Usefully, the acenaphtho[1,2-b]quinoxaline sulfoderivatives described herein can individually or as a system, mixture or composition act as an optically isotropic or anisotropic polarizing and/or phase-retarding film or material. An exemplary composition of such an optically isotropic or anisotropic film, for example, includes, but not limited to, at least two sulfoderivatives of the general structural formula disclosed herein with at least two different substituents X and/or Y or at least one kind of substituents at two different locations.

The above described combinations describe some aspects of the technical objectives of the present invention by, in particular, yielding anisotropic films or materials comprising individual acenaphtho[1,2-b]quinoxaline sulfoderivatives accordingly to, but not limited to, the general structural formula disclosed herein or systems comprising mixtures of compounds of these structural formulas without or without organic compounds including, but not limited to, colorless organic compounds, organic dye, surfactants, stabilizers, additives, modifiers, polymers and/or plasticizers.

In particular embodiments, films, LLC systems, materials, mixtures, combinations and blends of the present invention comprise at least one acenaphtho[1,2-b]quinoxaline sulfoderivative of the general structural formula disclosed herein with or without organic dyes, organic compounds, surfactants, additives, modifiers, stabilizers or plasticizers. In other embodiments, acenaphtho[1,2-b]quinoxaline sulfoderivatives of the present invention include any structure the general structural formula disclosed herein with or without organic dyes, organic compounds, surfactants, additives, modifiers, stabilizers or plasticizers.

Method for Forming Optical Films

In another aspect, the present invention provides methods for preparing anisotropic film by depositing a LLC system corresponding to those disclosed herein onto a substrate.

The acenaphtho[1,2-b]quinoxaline sulfoderivatives of the present invention are capable of forming stable lyotropic liquid crystal (LLC) systems.

When dissolved in water or any suitable solvent, the molecules of acenaphtho[1,2-b]quinoxaline sulfoderivatives of the general structural formula disclosed herein and/or mixtures thereof form anisometric (rod-like) supramolecules in which molecules are packed in a parallel manner, much like a deck of playing cards. As the concentration of supramolecules in solution increases, natural ordering of the anisometric supramolecules proceeds, leading to nematic lyotropic mesophase formation as the system becomes liquid crystalline (colloid system). Supramolecules function as the kinetic units of the system. The concentration at which the transition to a LC state occurs depends on the ratio of acenaphtho[1,2-b]quinoxaline sulfoderivatives which lies in the range of approximately 3% to 60% by mass. The LC state is easily fixed with by standard methods, such as, for example, polarization microscopy.

LC is the pre-ordered state of the system, from which, during alignment of the supramolecular complexes and subsequent removal of the solvent, immerges the anisotropic film. LC solutions (systems) of individual acenaphtho[1,2-b]quinoxaline sulfoderivatives of the general structural formula disclosed herein, as well as their mixtures, may be deposited on a substrate surface and aligned on it using any known method, such as for example those disclosed in U.S. Pat. Nos. 5,739,296, 6,174,394 and 6,563,640, the disclosures of which are hereby incorporated by reference in their entirety. For example, the desired molecular orientation may be obtained by applying shear stress, or gravitational or electric or magnetic fields. For better substrate surface wetting and improvement of LC solution rheological properties, a solution may be doped with modifying additives, such as for example plasticizing water-soluble polymers and/or anion-active or nonionic surfactants. Low-molecular weight water-soluble compounds may alternatively be used. Such additives are chosen from those compounds that do not destroy the alignment of a LC solution.

Upon solvent removal from the oriented film, an anisotropic film with a thickness of approximately 0.1 to 1.2 microns is formed. Within the obtained layer, planes of molecules are parallel to each other and so form the three-dimensional crystal in at least a part of the layer. Such layer possesses high degree of anisotropy and high refraction index for at least one direction. The difference of refraction indices along and across alignment direction in the visible spectral region is in the range of approximately 0.1 to 0.6. Such high birefringence was not achieved for the known polymer retarders. Thus, the retardation value of double-refraction films based on the present invention is approximately 10–100 times higher than what is achievable with widely used polymer materials with the same thickness.

In one embodiment, the method of obtaining thin anisotropic transparent films from the LLC formed by supramolecules comprises the following steps:

deposition of this LLC onto the substrate (or a functional layer of a LCD, or one of the layers of the multilayered structure); the said LLC possesses thixotropic properties, for that the LLC must be at a certain temperature and have certain concentration of the dispersion phase;

converting the deposited LLC into the state of increased fluidity via any external impact, which provides a decrease of viscosity of the system (this may be heating, deformation by shearing, etc.); external impact may continue during the entire subsequent process of alignment or have the necessary duration so that the LLC does not have the time to relax into the state with increased viscosity during alignment;

external orienting influence on the LLC, which may be implemented mechanically as well as with any other method; the degree of this influence must be sufficient so that the kinetic units of the LLC receive the necessary orientation and form the structure, which will be the basis for the future crystal lattice in the forming layer;

conversion of the oriented region of the forming film from the state with lowered viscosity, which was achieved with the primary external influence, into the state with the original or higher viscosity of the system; this is performed in such a way that there is no disorientation of the structure in the forming film and so as to avoid appearance of defects of the surface of the layer;

concluding operation, is the process of removing the solvent from the forming film, during which the anisotropic film is formed. Desirably, although not necessary, the anisotropic film of the present invention is at least partially crystalline. The optically anisotropic film exhibits an interplanar spacing in a crystal lattice unit in the range of approximately 3.1–3.7 Å along one of the optical axes. Standard methods for determining distances at the atomic level include, but not limited to, X-ray diffraction.

Synthesis of Acenaphtho[1,2-b]quinoxaline Sulfoderivatives

The present invention provides a method for synthesizing acenaphtho[1,2-b]quinoxaline sulfoderivatives of structures I–VIII.

For example, sulfoderivatives of the general structural formula, wherein M=H, designated hereinbelow as, X can be formed utilizing various methods known to the skill artisan. In a non-limited example, the sulfoderivatives of the present invention can be synthesized by the sulfonation of acenaphtho[1,2-b]quinoxaline or its derivatives IX with, but not limited to, sulfuric acid, oleum, chlorosulfonic acid, or combinations thereof, at different concentrations and temperature according to scheme 1:

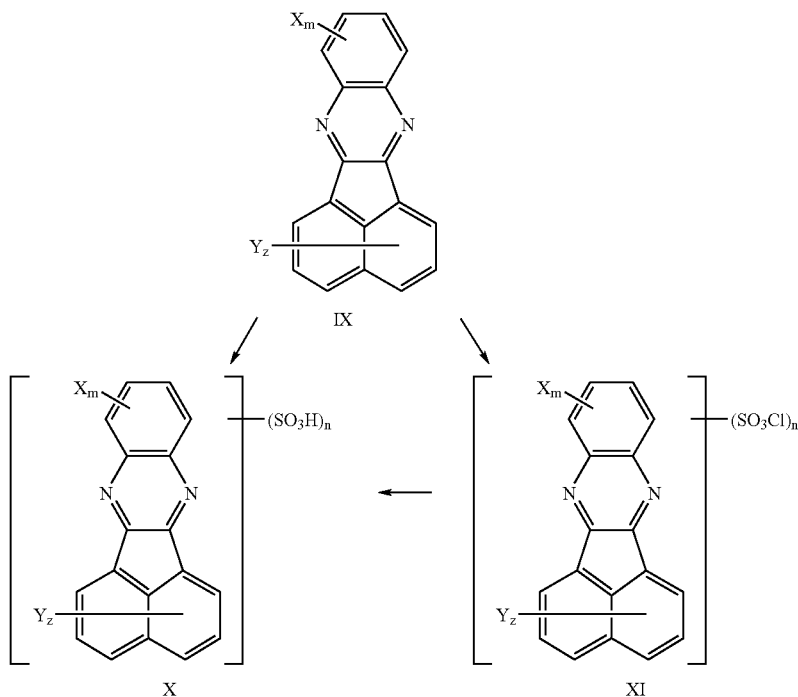

Scheme 1 wherein n is an integer in the range of 1 to 4, m is an integer in the range of 0 to 4, z is an integer in the range of 0 to 6, such that the equation $m+z+n \leq 10$, and X and Y are individually selected from the group consisting of $CH_3$, $C_2H_5$, $OCH_3$, $OC_2H_5$, Cl, Br, OH, $OCOCH_3$, $NH_2$, $NHCOCH_3$ and $NO_2$.

Now referring to scheme 1, following the sulfonation of acenaphtho[1,2-b]quinoxaline or its derivative IX, sulfo-derivatives of a general formula X can be synthesized via hydrolysis of the derivatives XI In typical sulfonation reactions of acenaphtho[1,2-b]quinoxaline and its derivatives, reactions can proceed in an organic solvent or neat, e.g., using the sulfonating agent as the solvent.

Alternatively, as illustrated in scheme 2, acenaphtho[1,2-b]quinoxaline sulfoderivatives of the present invention can also be produced by a condensation reaction between acenaphthenequinone or its derivatives, for example, but not limited to, structural formula XII, with o-phenylenediamine or its derivatives, for example, but not limited to, structural formula XIII, to yield one contemplated structure, e.g., structural formula XIV, of the present invention:

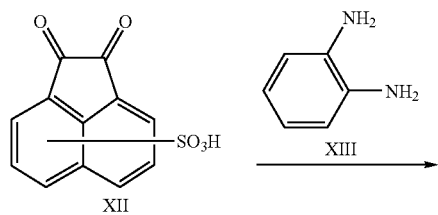

-continued

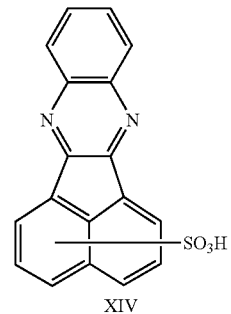

XIV

Still referring to scheme 2, although only one sulfonate group resides on structure XII, one or more sulfonates and/or X and Y groups could reside on structure XII prior to condensation of structures XII and XIII. Optionally, one or more sulfonates and/or X and Y groups could also reside on XIII instead of structure XII. Alternatively, both XII and XIII can be substituted with one or more sulfonate, X, Y or combinations thereof.

These and other embodiments for synthesizing acenaptho[1,2-b]quinoxaline and its derivatives thereof are further described herein below.

For example, in one aspect of the present invention, acenaptho[1,2-b]quinoxaline and its derivative thereof can be obtained from the condensation of a suitable pre-sulfonated acenaphthenequinone with a suitable pre-sulfonated ortho-phenylenediamine according to scheme 3:

Scheme 3

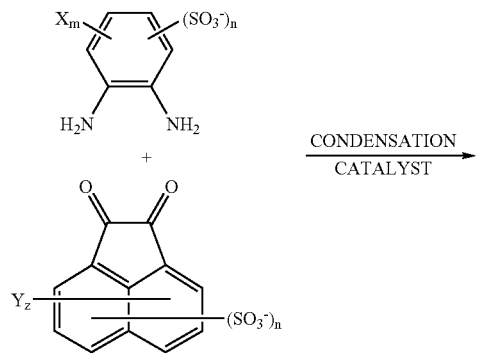

fonated phenylenediamine with a pre-sulfonated acenaphthenequinone as depicted in scheme 4:

Scheme 4

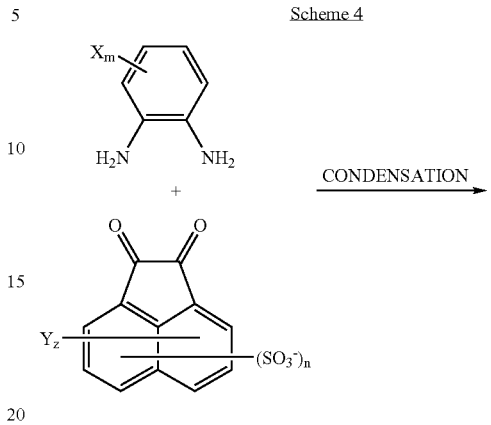

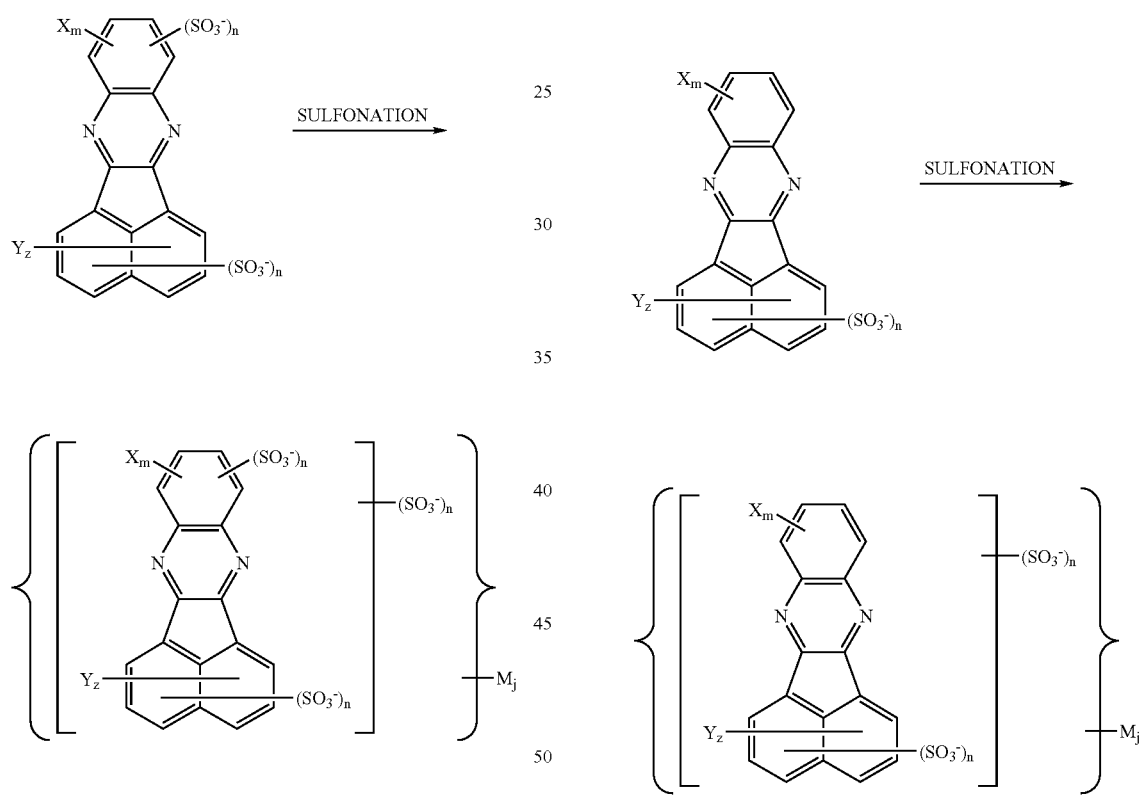

The condensation reaction can be accelerated or facilitated by the addition a catalyst such as, but not limited to, mineral, inorganic or organic acids, heat, drying agent, dehydrating agent, water scavenging agent, water absorbing agent, or a combination thereof.

Although not necessary, the condensation product can be further sulfonated by a variety of sulfonation reaction known to the skill artisan including, but not limited to, an electrophilic aromatic substitution, metal assisted nucleophilic reaction, Friedels-Craft reaction using $SO_3$ gas, oleum, thionyl chloride, sulfonyl chloride, fuming $H_2SO_4$, or combination thereof.

In a second aspect, acenaphtho[1,2-b]quinoxaline sulfoderivatives can be synthesized by condensing a non-sul- Optionally, the condensation product can be further sulfonated by a variety of sulfonation reaction known to the skill artisan including, but not limited to, an electrophilic aromatic substitution, metal assisted nucleophilic reaction, Friedels-Craft reaction using $SO_3$ gas, oleum, thionyl chloride, sulfonyl chloride, fuming $H_2SO_4$, or combination thereof.

In the third aspect, derivatives of acenaphtho[1,2-b]quinoxaline can synthesized by condensing a pre-sulfonated phenylenediamine with a non-sulfonated acenaphthenequinone as illustrated in scheme 5:

Scheme 5

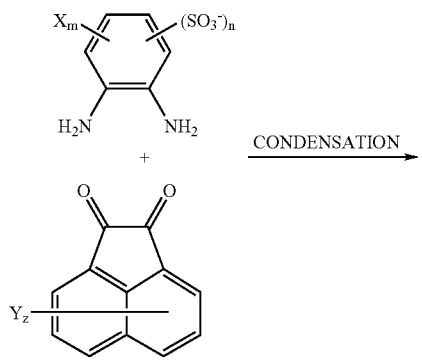

Scheme 6

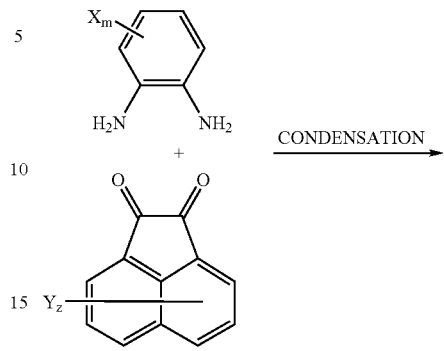

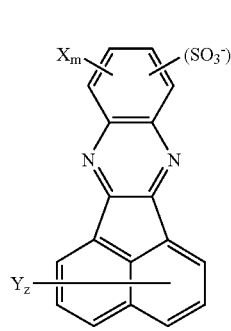

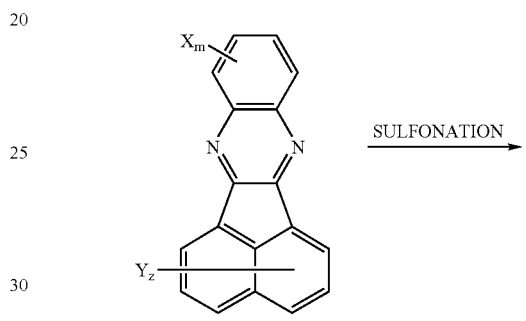

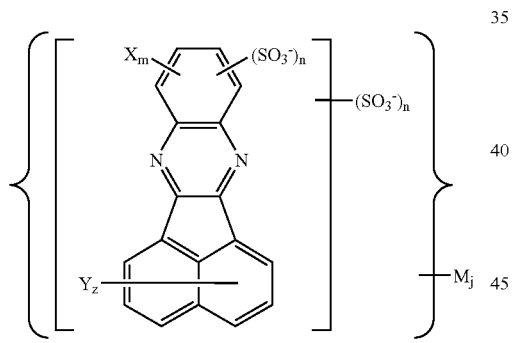

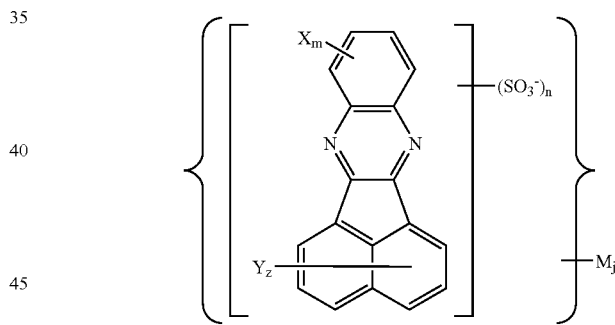

Optionally, the condensation product can be further sulfonated by a variety of sulfonation reaction known to the skill artisan including, but not limited to, an electrophilic aromatic substitution, metal assisted nucleophilic reaction, Friedels-Craft reaction using $SO_3$ gas, oleum, thionyl chloride, sulfonyl chloride, fuming $H_2SO_4$, or combination thereof.

Alternatively, now referring to scheme 6, derivatives of acenaphtho[1,2-b]quinoxaline is synthesized by a two step method involving the condensation a non-sulfonated phenylenediamine with a non-sulfonated acenaphthenequinone-the phenylenediamine, subsequently follow by a sulfonation reaction such as, but not limited to, an electrophilic aromatic substitution, metal assisted nucleophilic reaction, Friedels-Craft reaction using $SO_3$ gas, oleum, thionyl chloride, sulfonyl chloride, fuming $H_2SO_4$, or combination thereof. For example:

Suitable phenylenediamines can be purchased from Sigma-Aldrich (Milwaukee, Wis., www.sigmaaldrich.com) or Dynamic Synthesis (New Jersey, N.Y., www.dynamic-synthesis.com). Alternatively, the phenylenediamines from either Aldrich or Dynamic Synthesis can be chemically manipulated to provide the desired substituted phenylenediamine derivatives. Similarly, acenaphthenequinone can be purchased from Sigma Aldrich (Milwaukee, Wis., www.sigmaaldrich.com) or chemically manipulated to provide the desired substituted acenaphthenequinone. Methods for chemically manipulating phenylenediamine and acenaphthenequinone are described in, for example, Larock et al., Comprehensive Organic Transformations, $2^{nd}$ Ed., Wiley, New York, N.Y. (1999), which is incorporated herein in entirety by reference.

Separation and/or purification of individual acenaphtho [1,2-b]quinoxaline sulfoderivatives can be fractioned from their mixtures in solution by fractional crystallization/precipitation. Optionally, the individual sulfoderivatives can be separate and/or purified by ion-exchange columns, column chromatography, high pressure liquid chromatography, selective crystallization, derivatization-separation, gel electrophoresis, centrifugation, or combination thereof.

Experimental

A number of experiments were conducted according the method and system of the present invention. These experiments are intended for illustration purposes only, and are not intended to limit the scope of the present invention in any way.

EXAMPLE 1

Acenaphtho[1,2-b]quinoxaline-2-sulfonic Acid was Synthesized by Sulfonation of acenaphtho[1,2-b]quinoxaline Acenaphtho[1,2-b]quinoxaline (10 g) was charged into 10% oleum (70 ml) and stirred for 15 hours at room temperature. The reaction mass was diluted with water (203 ml). The final sulfuric acid concentration was 40%. The precipitate was filtered and washed with acetic acid (~30 ml). The filtered precipitate was air dried at 120° C. The process yielded 10.1 g of acenaphtho[1,2-b]quinoxaline-2-sulfoacid. $^1$H NMR (Bruker AMX-400, DMSO-$d_6$, δ, ppm): 7.77 (q, 2H, 3 Hz); 7.89 (t, 1H, 8 Hz); 8.1–8.15 (m, 2H); 8.30 (dd, 2H, 7 Hz); 8.58 (s, 1H); 8.66 (s, 1H). The electron spectrum (spectrometer UV/VIS Ocean PC 2000, aqueous solution): $\lambda_{max1}$=245 nm and $\lambda_{max2}$=320 nm. Elemental analysis calculated for $C_{18}H_{10}N_2O_3S$: C, 64.66; H, 3.01; N, 8.38; found: C, 64.19; H, 2.88; N, 8.45.

EXAMPLE 2

Acenaphtho[1,2-b]quinoxaline-2,5-disulfonic Acid was Synthesized by Sulfonation of acenaphtho[1,2-b]quinoxaline Acenaphtho[1,2-b]quinoxaline (10 g) was charged into 10% oleum (49 ml), stirredfor 30 minutes and heated at 180–190° C. for 30 hours. The reaction mixture was then diluted with water (95 ml), and the formed precipitate was filtered and washed with acetic acid (~30 ml). The filtered cake was dried on air at 120° C. to yield 8.2 g of acenaphtho[1,2-b]quinoxaline-2,5-disulfonic acid. $^1$H NMR (Bruker AMX-400, DMSO-$d_6$, δ, ppm): 7.82 (q, 2H, 3 Hz); 8.18 (q, 2H, 3 Hz); 8.24–8.36 (broad s, 2H); 8.62 (s, 4H). Elemental analysis calculated for $C_{18}H_{10}N_2O_6S_2$: C, 52.17; H, 2.43; N, 6.76; found: C, 52.02; H, 2.35; N, 6.56.

EXAMPLE 3

Acenaphtho[1,2-b]quinoxaline-9-sulfonic acid Synthesized by the Condensation of 3,4-Diaminobenzenesulfonic Acid with Acenaphthenequinone 3,4-Diaminobenzene-4-sulfonic acid (15 g) was added to a suspension of acenaphthenequinone (15.9 g) in acetic acid (150 ml). The reaction mixture was refluxed for 12.5 h. The solid was separated, washed with acetic acid (30 ml) and dried on air at 120° C. for 3 h to yield the desired compound (19.2 g). $^1$H NMR (Bruker AMX-400, DMSO-$d_6$, δ, ppm): 7.81 (broad t, 2H); 8.07 (broad s, 2H); 8.14 (d, 2H, 8 Hz); 8.26 (q, 2H); 8.39 (broad s, 1H). The acidic proton was not observed.

EXAMPLE 4

A Composition and Film were Produced According to the Present Invention and Analyzed to Determine the Film's Optical Characteristics To 65 g of deionized water, a mixture of sulfoderivatives of acenaphtho[1,2-b]quinoxaline (12 g) was added with stirring at 20° C. Then, 5.3 ml of 25% aqueous ammonia solution was added, and the mixture was stirred until complete dissolution. The solution was concentrated on rotary evaporator by 30% of initial volume and coated onto a glass plate surface with a Mayer rod #2.5 at a linear rate of 15 mm s$^{-1}$ at 20° C. with a relative humidity of 65%. The film was dried at 20° C. at 65% humidity.

Figure 4:
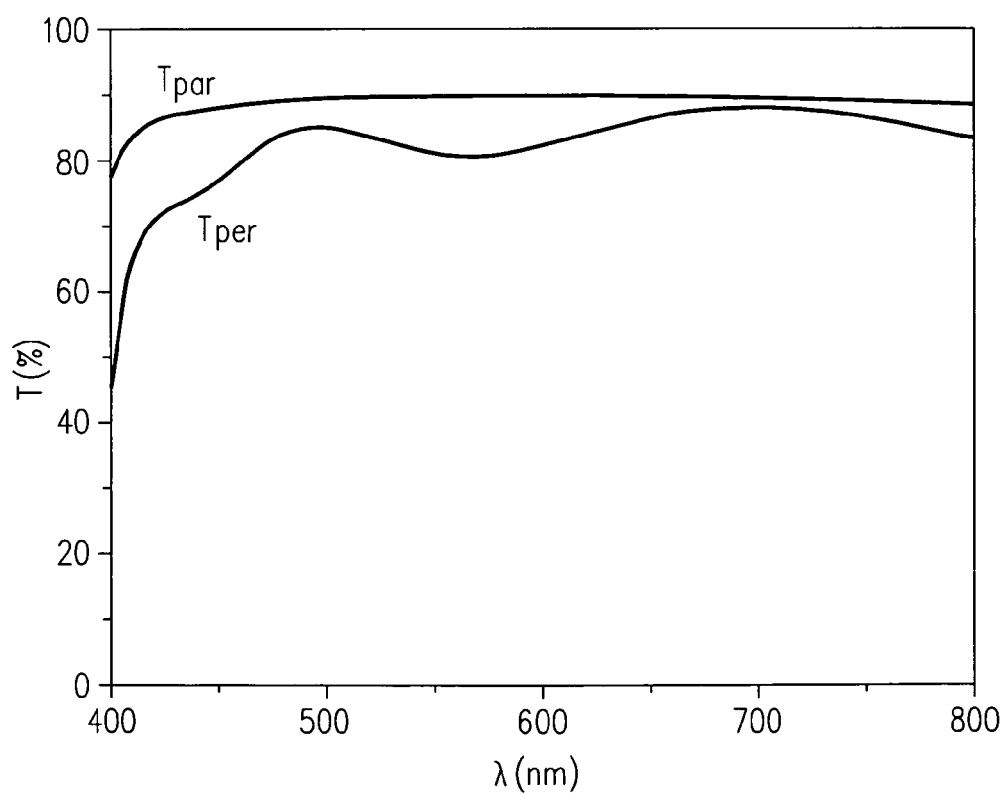
FIG. 4 is a transmission spectrum illustrating the change in transmission coefficients ($T_{par}$, $T_{per}$) over a specific range of wavelengths for a film fabricated from one contemplated acenaphtho[1,2-b]quinoxaline sulfonate system of the present invention.

Now referring to FIG. 4, to determine the optical characteristics of the film, transmission spectra were measured in polarized light in the wavelength range of 400–800 nm using a Cary-500 spectrophotometer. The measured optical transmission of the film with linearly polarized light graphs the transmission spectra parallel ($T_{par}$) and perpendicular ($T_{per}$) to the coating direction. Still referring to FIG. 4, the film shows very little absorbance in the visible spectral range and, in particular, above 430 nm.

Similarly, now referring back to FIG. 2, refractive indices parallel ($n_e$) and perpendicular ($n_o$) and absorption coefficients parallel ($k_e$) and perpendicular ($k_o$) each with respect to the alignment direction was calculated. The produced film is optically anisotropic and exhibits high retardation characteristic An increasing from 0.25 up to 0.55 in the visible spectral range. The low values of absorption coefficients $k_o$ and $k_e$ corroborate the high transparency of the film.

Figure 5:
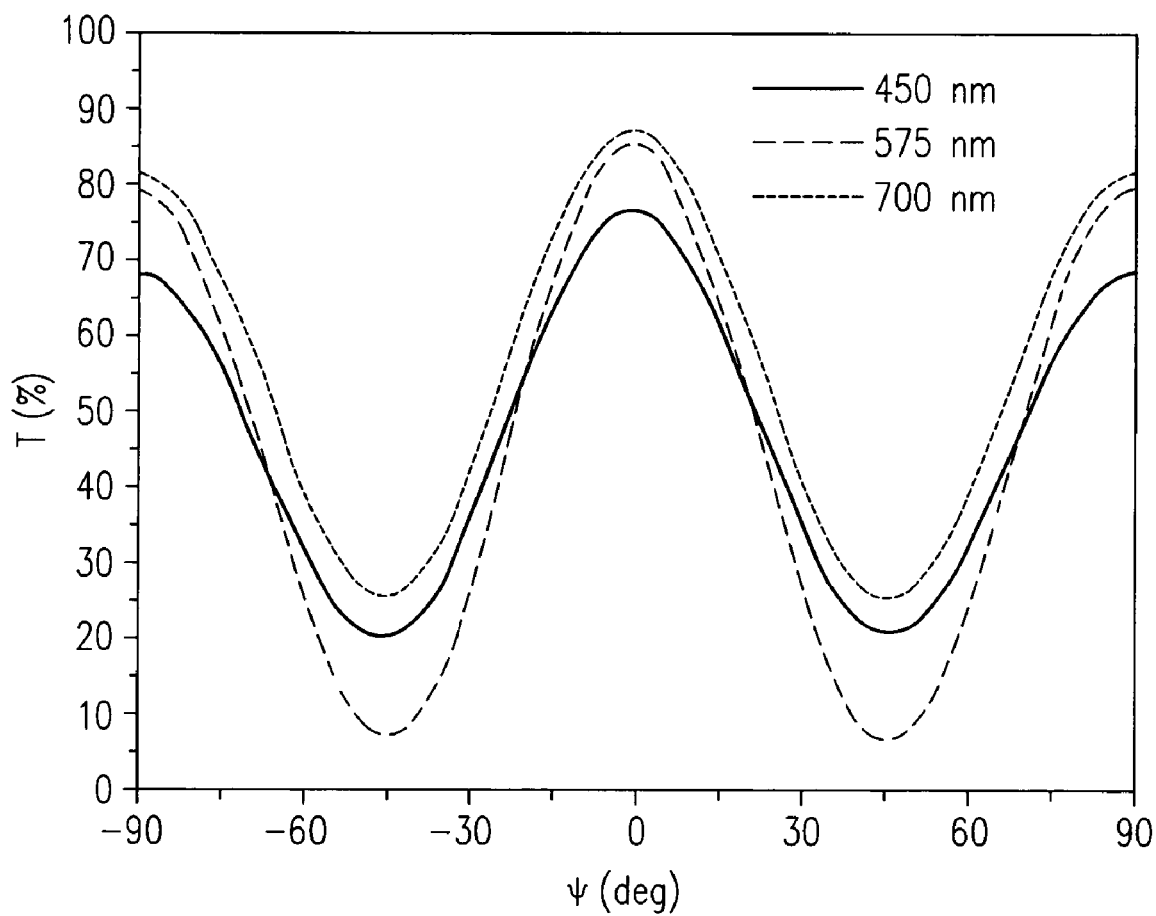
FIG. 5 depicts the relationship between transmission versus rotating angle at wavelengths 450 nm, 575 nm, and 700 nm for an optically anisotropic film placed between parallel polarizers.

Now referring to FIG. 5, the transmission spectra versus the rotating angle at various wavelengths, e.g., 450 nm, 575 mn, and 700 nm, are provided for an optically anisotropic film placed between parallel polarizers. The alignment direction corresponds to the angle 0°. These measurements allow us to observe the rotation of the plane of polarization when polarized light passes through the film.

The foregoing description of the embodiments of the invention has been presented for the purpose of illustration and description. They are not intended to be exhaustive or to limit the invention to the precise forms disclosed, and obviously many modifications, embodiments, and variations are possible in light of the above teaching. It is also intended that the scope of the invention by defined by the Claims and Examples appended hereto and their equivalents.

What is claimed is:

1. An acenaphtho[1,2-b]quinoxaline sulfoderivative of the general structural formula:

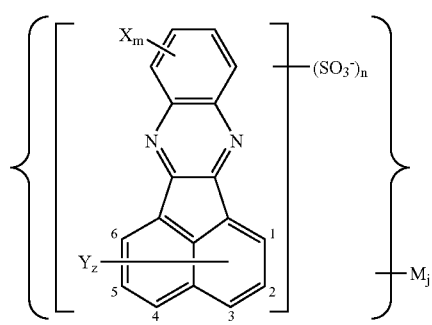

wherein:

n is an integer in the range of 1 to 4;

m is an integer in the range of 0 to 4;

z is an integer in the range of 0 to 6 and m+z+n≦10; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;

M is a counterion; and j is the number of counterions in the molecule, with the proviso that when n=1 and $SO_3$— occupies position 1, then m ≠0 or z ≠0.

2. The acenaphtho[1,2-b]quinoxaline sulfoderivative of claim 1 wherein the structural formula is chosen from the group consisting of structures I, IIA–VIII:

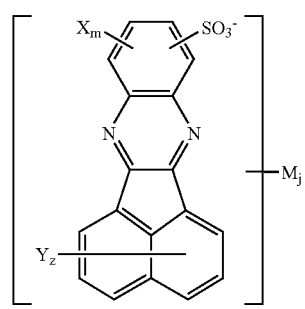

I wherein:

m is an integer in the range of 0 to 3, and z is an integer in the range of 0 to 6;

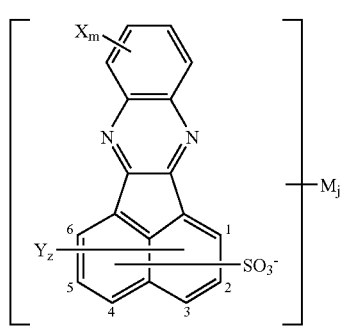

IIA wherein:

m is an integer in the range of 0 to 4, and z is an integer in the range of 0 to 5;

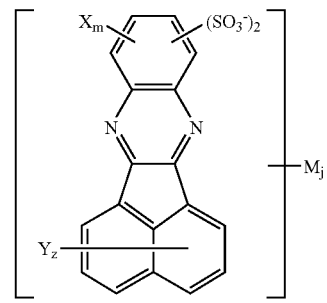

III wherein:

m is an integer in the range of 0 to 2, and z is an integer in the range of 0 to 6;

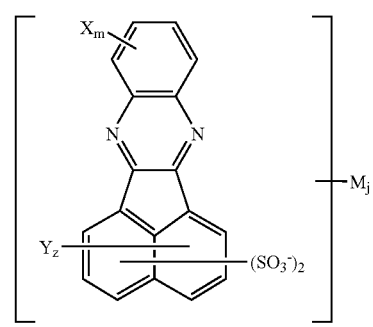

IV wherein:

m is an integer in the range of 0 to 4, and z is an integer in the range of 0 to 4;

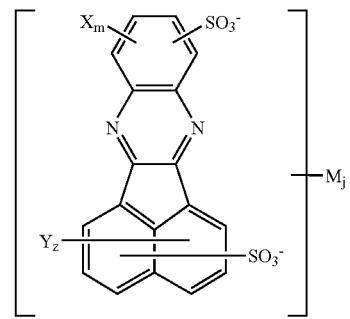

V wherein:

m is an integer in the range of 0 to 3, and z is an integer in the range of 0 to 5;

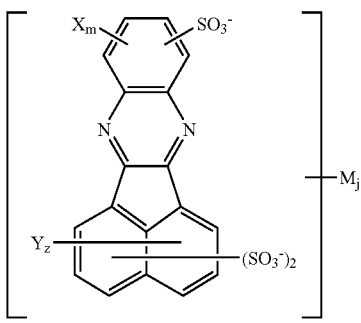

VI wherein:
m is an integer in the range of 0 to 3, and z is an integer in the range of 0 to 4;

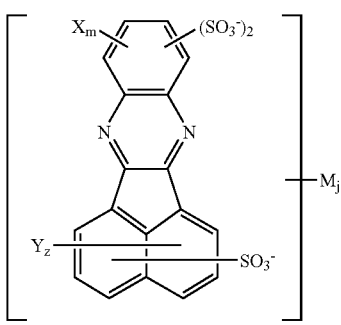

VII wherein:
m is an integer in the range of 0 to 2, and z is an integer in the range of 0 to 5;

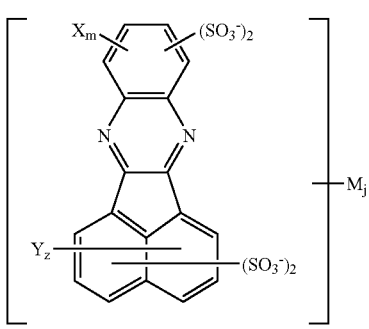

VIII wherein:
m is an integer in the range of 0 to 2, and z is an integer in the range of 0 to 4; and
wherein for each structures I, IIA–VIII:
X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;
M is a counterion; and
j is the number of counterions in the molecule.

3. The acenaphtho[1,2-b]quinoxaline sulfoderivative of claim 1 wherein said derivative is capable of forming a lyotropic liquid crystal system.

4. The acenaphtho[1,2-b]quinoxaline sulfoderivative of claim 1 wherein said derivative is capable of forming an optically isotropic or anisotropic film.

5. A lyotropic liquid crystal system comprising at least one acenaphtho[1,2-b]quinoxaline sulfoderivative of the general structural formula:

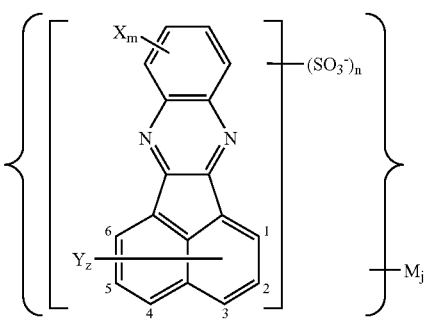

wherein:
n is an integer in the range of 1 to 4;
m is an integer in the range of 0 to 4;
z is an integer in the range of 0 to 6 and $m+z+n \leq 10$; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;
M is a counterion; and
j is the number of counterions in the molecule.

6. The lyotropic liquid crystal system of claim 5 comprising a mixture of said acenaphtho [1,2-b]quinoxaline sulfoderivatives.

7. The lyotropic liquid crystal system of claim 6 comprising a mixture of acenaphtho[1,2-b]quinoxaline sulfoderivatives wherein:
monosulfoderivatives of structures of claim 5 at n=1 are present in a concentration range of approximately 0% to 99% by mass;
disulfoderivatives of structures of claim 5 at n=2 are present in a concentration range of approximately 0% to 99% by mass;
trisulfoderivatives of structures of claim 5 at n=3 are present in a concentration range of approximately 0% to 30% by mass; and
tetrasulfoderivatives of structure of claim 5 at n=4 are present in a concentration range of approximately 0% to 20%;
wherein the total amount of the mono-, di-, tri-, and tetra-sulfoderivatives is 100% by mass.

8. The lyotropic liquid crystal system of claim 5 wherein said lyotropic liquid crystal system is based on a mixture of water and an organic solvent miscible with water.

9. The lyotropic liquid crystal system of claim 5 wherein the content of acenaphtho[1,2-b]quinoxaline sulfoderivatives is in the range of approximately 3% to 60% by mass.

10. The lyotropic liquid crystal system of claim 9 wherein the content of acenaphtho[1,2-b]quinoxaline sulfoderivatives is in the range of approximately 7% to 30% by mass.

11. The lyotropic liquid crystal system of claim 5 further comprising up to approximately 30% by mass of surfactants.

12. The lyotropic liquid crystal system of claim 5 further comprising up to approximately 30% by mass of plasticizers.

13. The lyotropic liquid crystal system of claim 5 further comprising at least one water-soluble organic compound capable of forming a common lyotropic liquid crystal system with said at least one acenaphtho[1,2-b]quinoxaline sulfoderivative of claim 5.

14. The lyotropic liquid crystal system of claim 6 comprising at least two sulfoderivatives having at least two different substituents Xm and/or Yz or at least one kind of substituent at two different location.

15. An optically anisotropic film comprising at least one acenaphtho[1,2-b]quinoxaline sulfoderivative of the general structural formula:

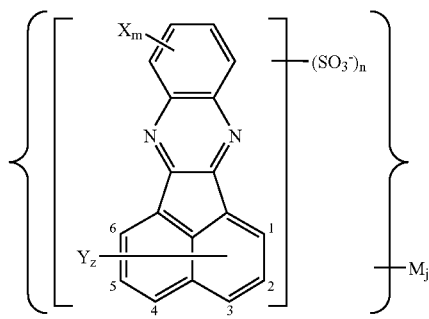

wherein:
n is an integer in the range of 1 to 4;
m is an integer in the range of 0 to 4;
z is an integer in the range of 0 to 6 and m+z+n≦10; X and Y are individually selected from the group consisting of $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$;
M is a counterion; and
j is the number of counterions in the molecule.

16. The optically anisotropic film of claim 15 containing a mixture of said acenaphtho[1,2-b]quinoxaline sulfoderivatives.

17. The optically anisotropic film of claim 15 further comprising at least one additional organic compound.

18. A method of forming an anisotropic transparent film comprising the steps of:
dissolving an acenaphtho[1,2-b]quinoxaline sulfoderivatives of claim 5 in a suitable solvent for creating the lyotropic liquid crystal system of supramolecules;
applying (depositing) a layer of the lyotropic liquid crystal with supramolecules onto a substrate;
externally impacting the lyotropic liquid crystal system to lower the viscosity of the applied layer;
applying external orienting action on the lyotropic liquid crystal system to provide dominant orientation of supramolecular;
allowing the deposited lyotropic liquid crystal system with dominant orientation of the supramolecules to return to at least its initial value of viscosity, and drying said lyotropic liquid crystal system.

19. The method of claim 18, wherein the external orienting action is applied simultaneously with applying a layer of the liquid crystal.

20. The method of claim 18 wherein the dried lyotropic liquid crystal system is treated with solutions of bi- or tri-valent metal salts to make the transparent film water-insoluble.

21. The optically anisotropic film of claim 15 wherein said film is at least partially crystalline.

22. The optically anisotropic film of claim 15 wherein the interplanar spacing is in the range of approximately about 3.1–3.7 Å along one optical axis.

23. The anisotropic film of claim 15 comprising at least two said acenaphtho[1,2-b]quinoxaline sulfoderivatives having at least two different substituents.

24. The anisotropic film of claim 15 wherein said film is birefringent.

25. The anisotropic film of claim 15 wherein said film is polarizing.

26. A lyotropic liquid crystal system of claim 5 wherein the structural formula is chosen from the group consisting of structures I, IIA–VIII, and any combinations thereof:

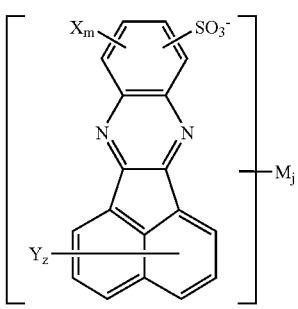

wherein:
m is an integer in the range of 0 to 3, and z is an integer in the range of 0 to 6;

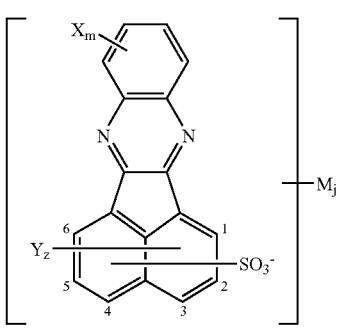

wherein:
m is an integer in the range of 0 to 4, and z is an integer in the range of 0 to 5;

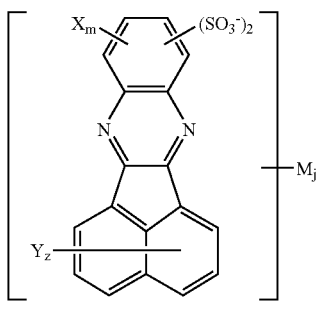

III wherein:

m is an integer in the range of 0 to 2, and z is an integer in the range of 0 to 6;

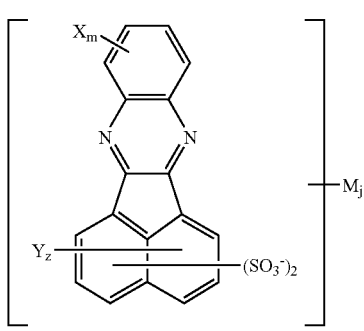

IV wherein:

m is an integer in the range of 0 to 4, and z is an integer in the range of 0 to 4;

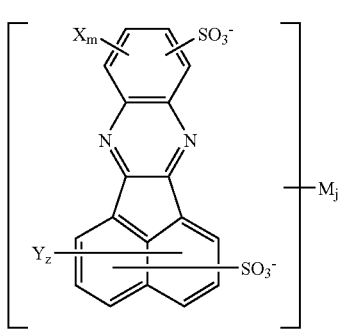

V wherein:

m is an integer in the range of 0 to 3, and z is an integer in the range of 0 to 5;

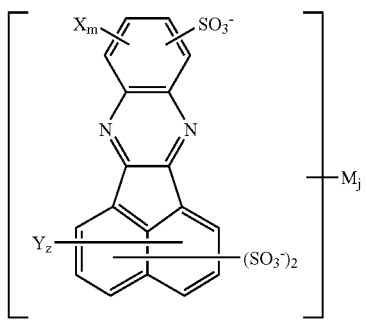

VI wherein:

m is an integer in the range of 0 to 3, and z is an integer in the range of 0 to 4;

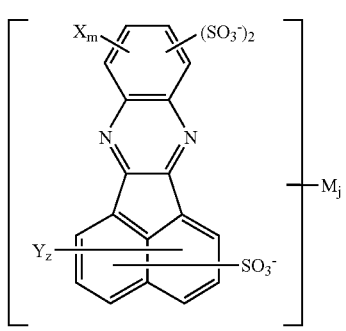

VII wherein:

m is an integer in the range of 0 to 2, and z is an integer in the range of 0 to 5;

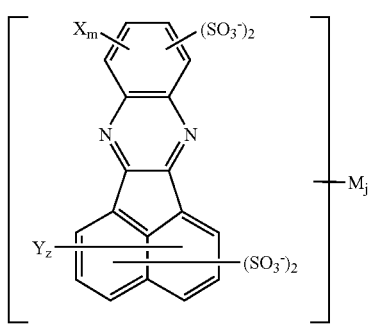

VIII wherein:

m is an integer in the range of 0 to 2, and z is an integer in the range of 0 to 4; and wherein for each structures I, IIA–VIII:

X and Y are individually selected from the group consisting of CH$_3$, C$_2$H$_5$, OCH$_3$, OC$_2$H$_5$, Cl, Br, OH, OCOCH$_3$, NH$_2$, NHCOCH$_3$, NO$_2$, F, CF$_3$, CN, OCN, SCN, COOH, and CONH$_2$;

M is a counterion; and j is the number of counterions in the molecule.

27. The optically anisotropic film of claim 15 wherein the structural formula is chosen from the group consisting of structures I, IIA–VIII, and any combinations thereof:

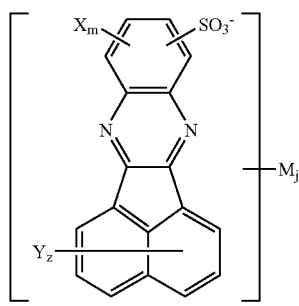
I wherein:
m is an integer in the range of 0 to 3, and z is an integer in the range of 0 to 6;

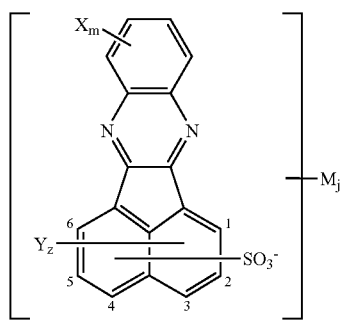
IIA wherein:
m is an integer in the range of 0 to 4, and z is an integer in the range of 0 to 5;

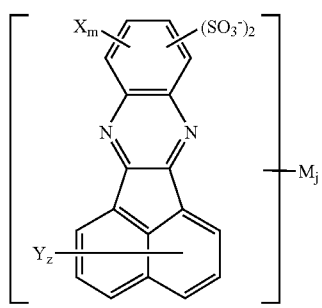
III wherein:
m is an integer in the range of 0 to 2, and z is an integer in the range of 0 to 6;

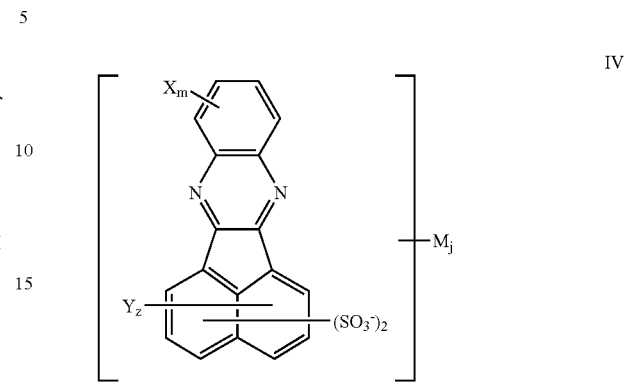
IV wherein:
m is an integer in the range of 0 to 4, and z is an integer in the range of 0 to 4;

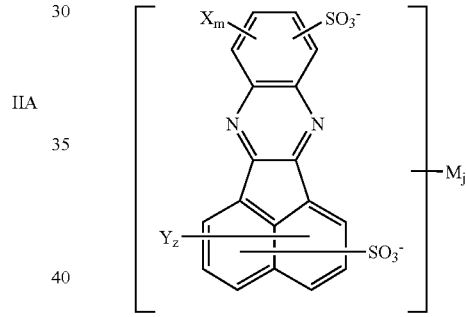
V wherein:
m is an integer in the range of 0 to 3, and z is an integer in the range of 0 to 5;

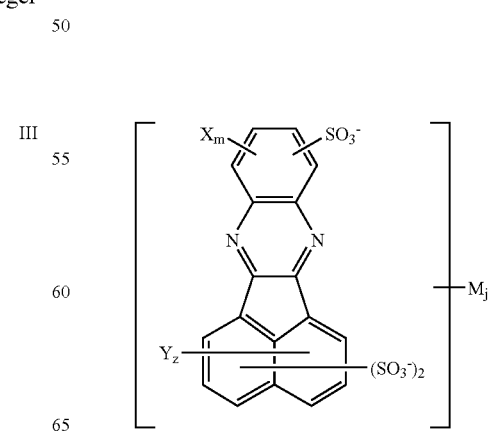
VI wherein:
m is an integer in the range of 0 to 3, and z is an integer in the range of 0 to 4;

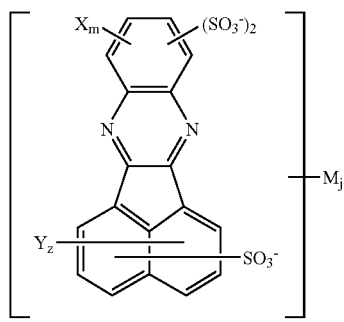

VII wherein:
m is an integer in the range of 0 to 2, and z is an integer in the range of 0 to 5;

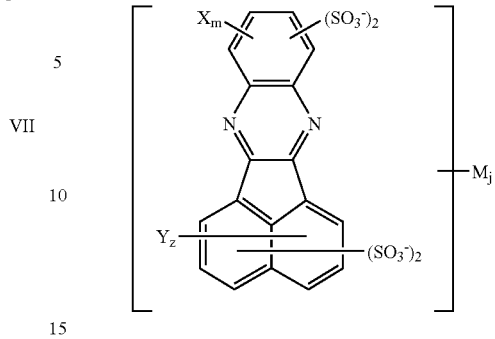

VIII wherein:
m is an integer in the range of 0 to 2, and z is an integer in the range of 0 to 4; and
wherein for each structures I, IIA–VIII:
X and Y are individually selected from the group consisting of $CH_3$, $C_2H_5$, $OCH_3$, Cl, Br, OH, $OCOCH_3$, $NH_2$, $NHCOCH_3$, $NO_2$, F, $CF_3$, CN, OCN, SCN, COOH, and $CONH_2$;
M is a counterion; and
j is the number of counterions in the molecule.

* * * * *